US00PP10325P

United States Patent [19]

Biehn et al.

[11] Patent Number: Plant 10,325

[45] Date of Patent: Apr. 14, 1998

[54] PEAR TREE NAMED 'BIEHN'

[76] Inventors: Nancy Biehn; Don Biehn, both of 1621 Orchard Rd., Hood River, Oreg. 97031

[21] Appl. No.: 792,065

[22] Filed: Feb. 3, 1997

[51] Int. Cl.[6] ..... A01H 5/00

[52] U.S. Cl. ..... Plt./36

[58] Field of Search ..... Plt./36

*Primary Examiner*—James R. Feyrer

*Attorney, Agent, or Firm*—Chernoff, Vilhauer, McClung & Stenzel

[57] ABSTRACT

A new variety of pear tree discovered as a limb mutation on a Bartlett pear tree, has fruit that ripens from two to three weeks later than the Bartlett, has russeting over its entire development and matures into fruit of a uniform golden color. The fruit has a higher sugar content than the Bartlett and a sweet, spicy, slightly cinnamon flavor.

4 Drawing Sheets

BACKGROUND AND SUMMARY OF THE INVENTION

The subject plant was discovered in 1979 as a limb mutation of a Bartlett pear tree, *Pyrus communis* L. C. V. 'Bartlett', growing in the inventors' orchard near Hood River, Oreg. The subject variety has been asexually reproduced by top working hardwood cuttings onto young Bartlett pear trees and by budding onto Anjou pear root stock at the same location. All subsequent clonal generations have been true to form in all respects. It is anticipated that this tree will be marketed under the trademark "Cinnamon".

The subject variety differs from its parent Bartlett pear in that its fruit ripens from two to three weeks later making the variety more characteristics of a winter pear. The fruit has a definite russet similar to that of a russet Bosc, but unlike a Bartlett. The russet appears very early in the life of the fruit, when just a fruitlet. The shape of the fruit of the subject variety is not like a Bartlett or like a Bosc. The subject variety has a more uniform, regular, ovate pyriform shape with more thickness in the neck than Bartlett or Bosc. The subject variety also has less length than the Bartlett or Bosc. As the fruit ripens the green ground color changes to a uniform golden russet. The fruit also does not have the surface bumpiness which is found in the Bartlett. Harvest dates and sugar content for the subject variety and the Bartlett for the years 1995 and 1996 are shown in the following tables.

| | Pressure (lbs) | Sugar (%) | Harvest Date |
|---|---|---|---|
| | 1995 | | |
| Biehn | 15.0 | 14.5–14.8 | Sept. 6 |
| Bartlett | 19.0 | 10.5–11.0 | Aug. 19 |
| | 1996 | | |
| Biehn | 17.5 | 12.0–12.8 | Sept. 23 |
| Bartlett | 19.0 | 10.5–11.0 | Aug. 28 |

While limited fruit production of the new variety prevents there being extensive data on storability, fruit stored until December 1996 was firm and showed no tendency toward breakdown or advanced maturity. Following five days of ripening the fruit softened to 4 lbs pressure which made it very edible. The flavor of the subject fruit is sweet, spicy, with a slight cinnamon flavor which is very unlike the Bartlett.

DETAILED DESCRIPTION OF THE VARIETY

Figure 1:
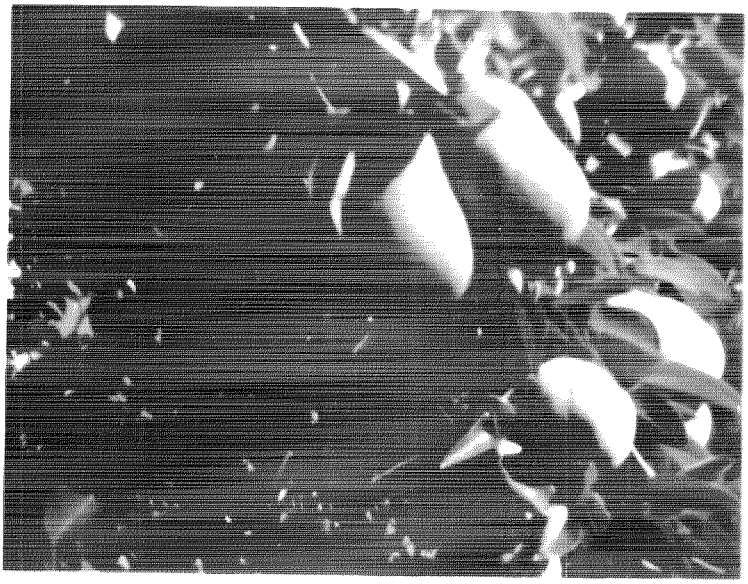
FIG. 1 shows the mother Bartlett pear tree with the normal fruit and the fruit of the subject variety growing together.
Figure 2:
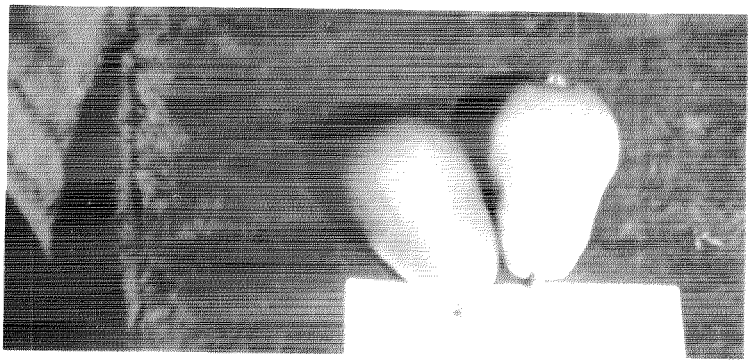
FIG. 2 shows the fruit of the subject variety on the left and of the Bartlett pear on the right.
Figure 3:
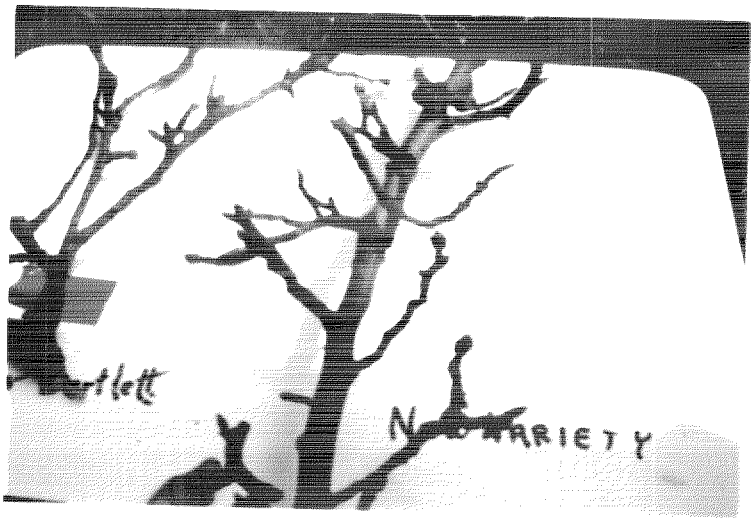
FIG. 3 shows the fruit buds and spurs of the subject variety on the right and of the Bartlett pear on the left.
Figure 4:
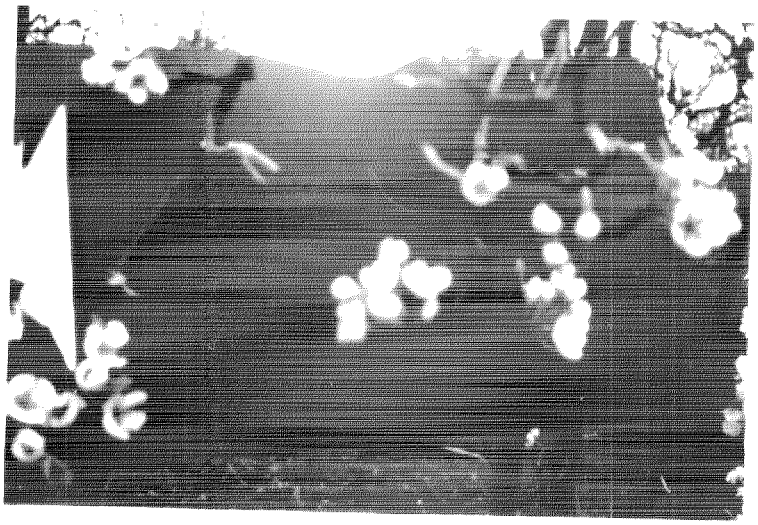
FIG. 4 shows the blooms of the subject variety on the right and of the Bartlett pear on the left.
Figure 6:
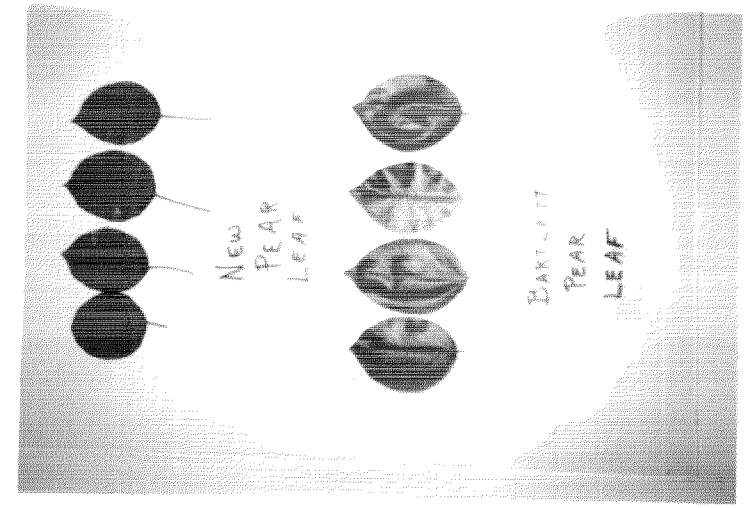
FIG. 6 shows the leaves of the subject variety on the top and of the Bartlett pear on the bottom.
Figure 5:
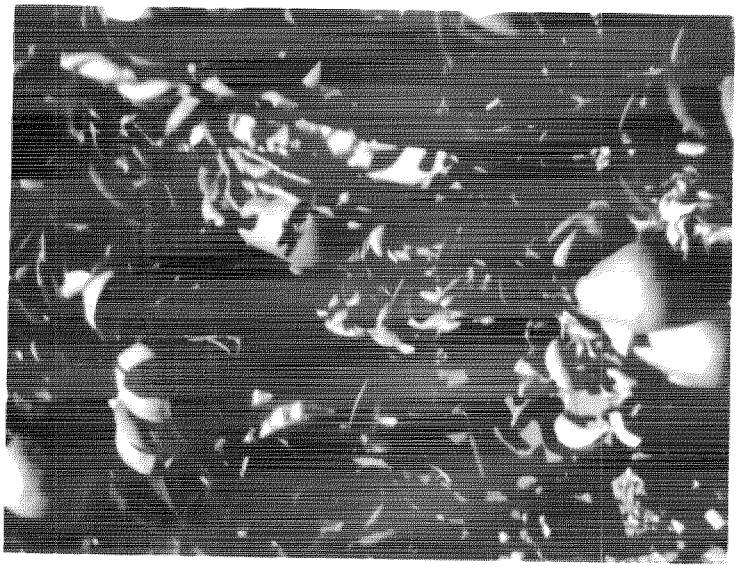
FIG. 5 shows the foliage of the mother Bartlett pear tree with the foliage of the subject variety growing alongside.
Figure 8:
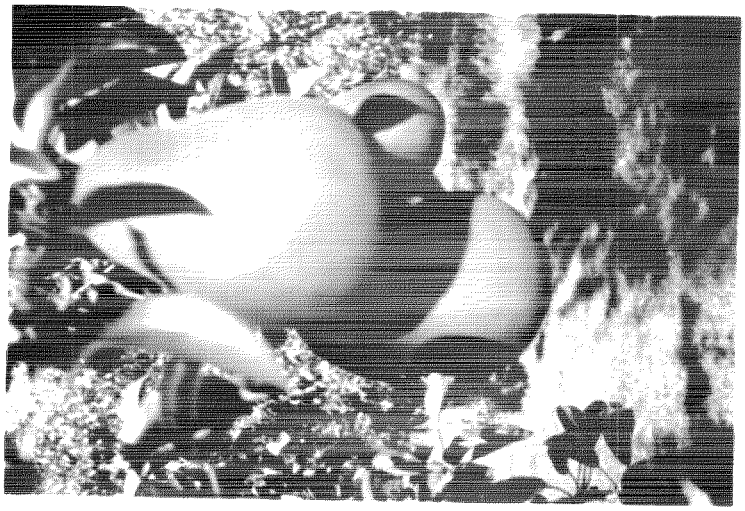
FIGS. 7 and 8 show fruit of the subject variety on the tree.
Figure 7:
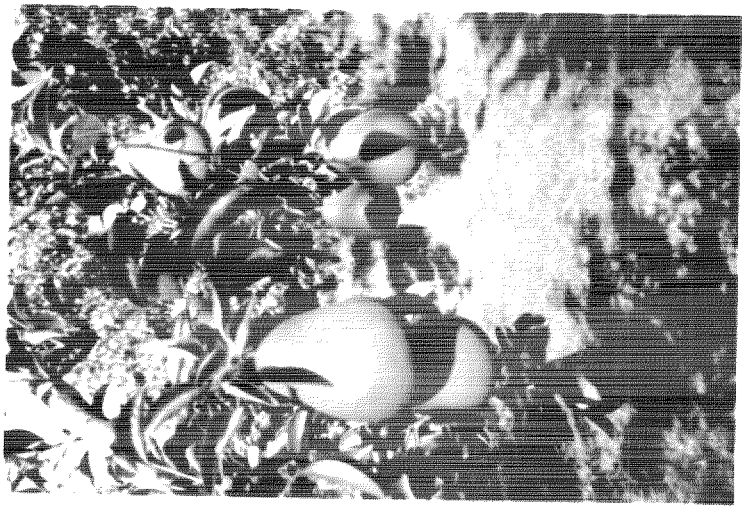

The following is a detailed description of the subject variety growing at the inventor's orchard near Hood River, Oreg. Color references are to the *Methuen Handbook of Color* by A. Kornerup and J. H. Wanscher.

DESCRIPTION OF VEGETATIVE CHARACTERISTICS

Technology is in accordance with *Modern Systemic Pomology* by Dr. Quentin Zielinski, Oregon Agriculture Experiment Station at Oregon State University.

Tree:

*Size.*—Unknown, as variety has not as yet been grown to maturity.

*Vigor.*—Moderately Vigorous.

*Form.*—Somewhat spreading, upright.

*Growth.*—Moderate.

*Hardiness.*—Very hardy.

*Production.*—Moderate too very productive.

*Bearing.*—Annual, regular late bearer.

Branches:

*Main branches.*—Stocky, spreading, thick and strong.

*Lateral branches.*—Spreading, lenticels prominent, olive brown (4-F5), with vertical dark grey streaks between nodes.

*Branchlets.*—Short internodes, tendency to spur readily.

*Lenticels.*—Distinct, rough, prominent and raised.

Leaves:

*Size.*—Medium small compared to Bartlett, average of 100 leaves; leaf length with stem 9.15 cms, w/o stems, 5.87 cms; leaf width, 4.2 cms.

*Form.*—Oval, symmetrical, tendency to fold along midrib.

*Apex.*—Abruptly pointed, short.

*Thickness.*—Medium, rib more prominent than Bartlett.

*Pubescence.*—None.

*Texture.*—Rough.

*Margin.*—Serrate, small teeth.

*Petiole.*—Medium, average length 3.27 cm.

*Color.*—Dark green (27 F8), underside medium green with grayish cast.

*Leaf buds.*—Form: Obtuse, pointed, smaller than Bartlett.

*Leaf scars.*—Less prominent than Bartlett.

Flowers:

*Blooming period.*—In Hood River, Oreg., April 10–25, which is similar to Bartlett.

*Size.*—Large, average diameter 1.20".

*Color.*—White, pale yellow center.

*Petals.*—Shape: Obovate, broad. Color: White. Pedicels: Long, pale green, length ½ to ¾". Fertility: Best with cross pollination.

*Flower buds.*—Size: Medium. Shape: Conical, plump and free.

Fruit:

*Fruitlet.*—Russets early in life of fruit.

*Date of first picking.*—In Hood River, Oreg., Sept. 1–25, 2–3 weeks after Bartlett.

*Retention.*—Appears to hang well.

*Size.*—Medium large; average length, 3.7"; width, 2.85"; L/D ratio 1.30.

*Form.*—Ovate pyriform, uniform, regular.

*Stem.*—Short, thick.

*Cavity.*—Obtuse, shallow, occasional fleshy ring.

*Calyx.*—Small, open.

*Lobes.*—Indistinct compared to Bartlett, united at base.

*Basin.*—Rounded, medium, shallow, smooth.

Skin:

*Texture.*—Fine, granualr, smooth russet.

*Color.*—Overall uniform yellow russet (4 C8 Curry Yellow).

*Dots.*—Small inconspicuous.

Flesh:

*Color.*—White.

*Texture.*—Tender, juicy, buttery, fine grain.

*Flavor.*—Sweet, spicy, slight cinnamon flavor.

*Eating quality.*—Best, desert quality.

*Core.*—Closed.

*Core lines.*—Clasping.

*Calyx tube.*—Funnel shape.

Seed:

*Size.*—Medium.

*Shape.*—Plump, obtuse, thick.

*Color.*—Medium to dark brown, white tip.

Use: Market, dessert.

Keeping quality: Longer than Bartlett.

We claim:

1. A new and distinct variety of pear tree, referred to as the Biehn cultivar, substantially as shown and described herein, characterized by its fruit ripening two to three weeks later than its parent, Bartlett, by its sweet, spicy, slightly cinnamon flavor and by its uniform golden russet color upon ripening.

* * * * *